(12) United States Patent
Duan et al.

(10) Patent No.: US 11,344,192 B2
(45) Date of Patent: May 31, 2022

(54) LIGHTING DEVICE AND ENDOSCOPE HAVING THE SAME

(71) Applicant: Ankon Medical Technologies (Shanghai) Co., LTD., Shanghai (CN)

(72) Inventors: Xiaodong Duan, Pleasanton, CA (US); Xu Wang, Shanghai (CN); Yi Yang, Shanghai (CN); Qinghu You, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 234 days.

(21) Appl. No.: 16/434,179

(22) Filed: Jun. 7, 2019

(65) Prior Publication Data

US 2019/0380568 A1 Dec. 19, 2019

(51) Int. Cl.
*A61B 1/06* (2006.01)
*G02B 23/24* (2006.01)
*A61B 1/05* (2006.01)

(52) U.S. Cl.
CPC .......... *A61B 1/0676* (2013.01); *A61B 1/0623* (2013.01); *G02B 23/2461* (2013.01); *A61B 1/05* (2013.01); *A61B 1/0638* (2013.01)

(58) Field of Classification Search
CPC ....... A61B 1/0676; A61B 1/0623; A61B 1/05; G02B 23/2461
See application file for complete search history.

(56) References Cited

U.S. PATENT DOCUMENTS

| | | | |
|---|---|---|---|
| 2005/0270775 A1* | 12/2005 | Harbers | G02B 27/1046 362/231 |
| 2016/0238923 A1* | 8/2016 | Tanaka | F21V 9/08 |
| 2017/0352161 A1* | 12/2017 | Ganapati | A61B 1/00011 |

\* cited by examiner

*Primary Examiner* — Alexandra L Newton
*Assistant Examiner* — Rynae E Boler
(74) *Attorney, Agent, or Firm* — Treasure IP Group, LLC

(57) ABSTRACT

An illuminating device and an endoscope having the same are described. The illuminating device includes a light source assembly, and the light source assembly includes a first light source, a diffusion sheet and a dichroic mirror. The diffusion sheet is disposed between the first light source and the dichroic mirror, and the diffusion sheet is used to diffuse light of the first light source.

12 Claims, 4 Drawing Sheets

LIGHTING DEVICE AND ENDOSCOPE HAVING THE SAME

CROSS REFERENCE TO RELATED APPLICATIONS

The present invention claims priority to Chinese Patent Application No. 201810615350.7 filed on Jun. 14, 2018, the contents of which are incorporated by reference herein.

FIELD OF INVENTION

The invention generally relates to a medical device, particularly refers to an illuminating device and an endoscope having the same.

BACKGROUND

With the development of science and technology, endoscopy as an minimally invasive method, has found extensive applications in a variety of fields such as human disease surveillance, industrial sealed chamber observation and remote observation and manipulation etc. The illuminating device is an essential component of an endoscope. In prior art, the illuminating device generally uses a halogen lamp, a xenon lamp or a high power LED as its light source.

However, when the halogen lamp and xenon lamp are used as the light source, too much heat is generated, so a heat insulating element needs to be added between the light source and the endoscope, resulting in low photoelectric conversion efficiency, hindering miniaturization of the illuminating device. High-power LEDs are often array-type white LEDs. Due to the limitation of Etendue, coupling devices such as tapered light guides that have convergence effects cannot conduct and illuminate the fibers, resulting in low coupling efficiency of the fibers, making the use of the light source inefficient.

In order to improve the utilization of light source, a laser can be used to remotely excite the phosphor to achieve white light illumination. However, according to the principle of phosphor excitation, if the excitation lights incident on the phosphor are not distributed uniformly, it tends to cause saturation of the phosphor at some positions, and under-saturation at other positions. If the excitation light intensity continues to increase, it is tends cause the phosphor in the saturated position to be quenched; to avoid the phosphor being quenched, it is only needed to reduce the intensity of the light source. This will undoubtedly reduce the luminance of the illuminating device, which in turn will reduce the quality of the entire endoscopic imaging, and thereby not conducive to use in the endoscope.

SUMMARY OF THE INVENTION

The present invention discloses an illuminating device, comprising: a light source assembly, the light source assembly comprising a first light source, a diffusion sheet and a dichroic mirror; wherein the diffusion sheet is disposed between the first light source and the dichroic mirror, and the diffusion sheet is used to diffuse light of the first light source.

In one embodiment, the light source assembly further comprises a first collimating lens, a second collimating lens, a fluorescent disc, and a reflective diffusion disc; wherein the dichroic mirror is disposed obliquely relative to the optical axis of the first light source; the fluorescent disc and the first light source are disposed at the same side of the dichroic mirror; the first collimating lens is disposed between the light paths of the fluorescent disc and the dichroic mirror; the reflective diffusion disc and the first light source are respectively located at opposite sides of the dichroic mirror; and the second collimating lens is arranged between the light paths of the dichroic mirror and the reflective diffusion disc.

In one embodiment, the first collimating lens and/or the second collimating lens is a cup-shaped lens in cross section, comprising a cylindrical cupped part at a side of the collimating lens facing the fluorescent disc or the reflective diffusion disc, wherein the bottom of the cupped part protruding toward the fluorescent disc or the reflective diffusion disc to form an arc surface.

In one embodiment, the light source assembly comprises a reflecting mirror and a fluorescent disc; wherein the dichroic mirror is disposed obliquely relative to the optical axis of the first light source; the fluorescent disc and the reflecting mirror are located at the other side of the dichroic mirror opposite to the first light source; the dichroic mirror comprises a small hole, the light passing through the small hole is reflected by the reflecting mirror to the fluorescent disc, and reflected by the fluorescent disc to the dichroic mirror with wavelength converted.

In one embodiment, the diffusion sheet comprises a first diffusion sheet and a second diffusion sheet; wherein the light source assembly further comprises a second light source and a fluorescent disc; the first diffusion sheet is arranged between the first light source and the dichroic mirror; the dichroic mirror is arranged obliquely relative to the optical axis of the first light source; the second light source, the second diffusion sheet and the fluorescent disc are arranged orderly along the optical path of the second light source; the second diffusion sheet is arranged between the second light source and the fluorescent disc; the second light source, the fluorescent disc and the dichroic mirror cooperate with each other so that the optical axis of the light emitted from the fluorescent disc with wavelength converted is perpendicular to the optical axis of the first light source.

In one embodiment, the illuminating device comprises a lens coupling assembly; wherein the lens coupling assembly is arranged orderly with the light source assembly; the light from the light source assembly enters the lens coupling assembly; the lens coupling assembly comprising a first converging lens, a light homogenizing rod and a conductive optical fiber; and the first converging lens, the light homogenizing rod and the conductive optical fiber are arranged orderly.

DETAILED DESCRIPTION

The present invention will be described in detail below with reference to the accompanying drawings and preferred embodiments.

The present invention provides an illuminating device and an endoscope using the same, in which the illuminating device enables the phosphor to be excited by a high-luminance light source, to produce long wavelength light with high energy density, which in turn increases the luminance of the white light illuminating device, and facilitate the miniaturization of the illuminating device, making it possible for the illuminating device described above to be used in the endoscope.

Figure 1:
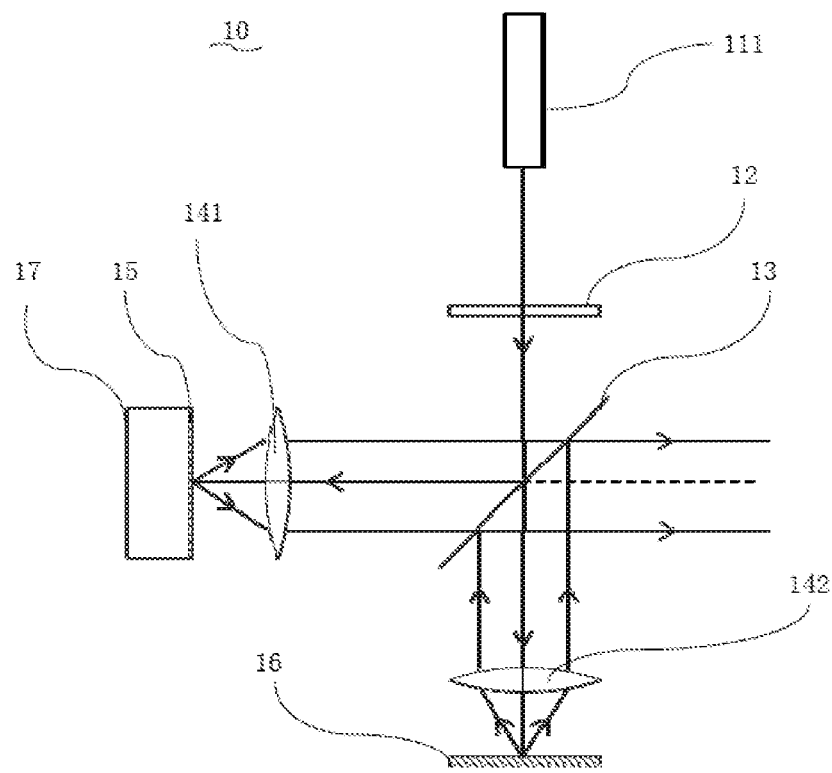
FIG. 1 shows a structural view of a light source assembly of the illuminating device according to the first embodiment of the invention.
Figure 2:
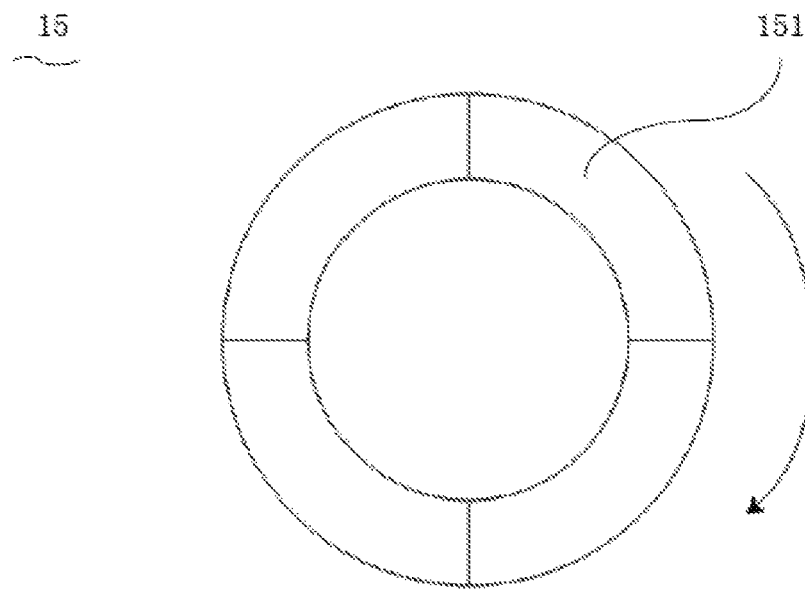
FIG. 2 show a structural view of a fluorescent disc of FIG. 1.
Figure 3:
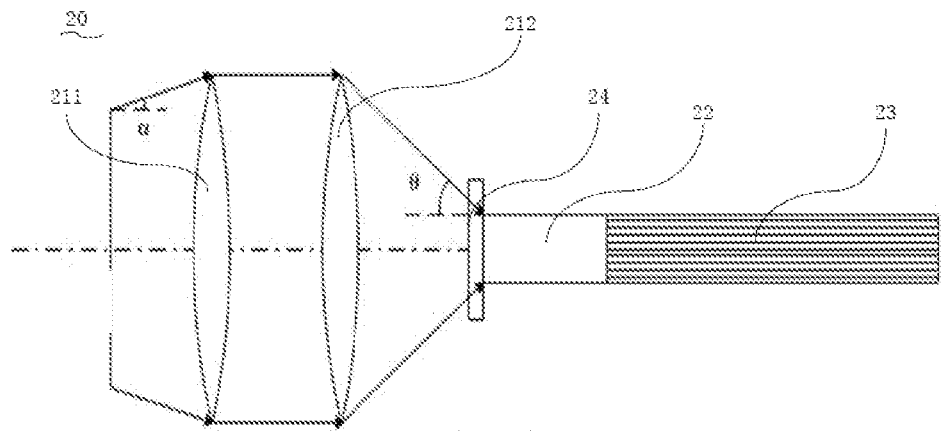
FIG. 3 shows a structural view of a lens coupling assembly of the illuminating device according to the first embodiment of the invention.

FIG. 1 shows a structural view of a light source assembly of the illuminating device according to the first embodiment of the invention, FIG. 2 show a structural view of a fluorescent disc of FIG. 1, and FIG. 3 shows a structural view of a lens coupling assembly of the illuminating device according to the first embodiment of the invention. As shown in FIGS. 1-3, the illuminating device 10 comprises a light source assembly 10 and a lens coupling assembly 20, and the light source assembly 10 and the lens coupling assembly 20 are arranged sequentially, and the light emitted from the light source assembly 10 passes through the lens coupling assembly 20 to a conductive optical fiber.

Referring to FIG. 1, the light source assembly 10 according to a first embodiment of the invention comprises a first light source 111, a diffusion sheet 12, a dichroic mirror 13, a first collimating lens 141, a fluorescent disc 15, a second collimating lens 142 and a reflective diffusion disc 16. The diffusion sheet 12 is disposed between the light paths of the first light source 111 and the dichroic mirror 13, and the dichroic mirror 13 is arranged obliquely relative to the optical axis of the first light source 111, at a preferred angle of −45° (The counterclockwise direction is taken as positive). The fluorescent disc 15 and the first light source 111 are arranged at the same side of the dichroic mirror 13, the first collimating lens 141 is arranged between the light paths of the fluorescent disc 15 and the dichroic mirror 13, and the optical axis of the first collimating lens 141 is perpendicular to the optical axis of the first light source 111. The reflective diffusion disc 16 and the first light source 111 are respectively arranged at opposite sides of the dichroic mirror 13, and the second collimating lens 142 is arranged between the light paths of the dichroic mirror 13 and the reflective diffusion disc 16, and the optical axis of the second collimating lens 142 is on the same straight line as the optical axis of the first light source 111.

In the embodiment, the first light source 111 is a semiconductor laser emitter, preferably a 450 nm blue laser. The light emitted from the first light source 111 passes through the diffusion sheet 12 and reaches the dichroic mirror 13.

Figure 4:
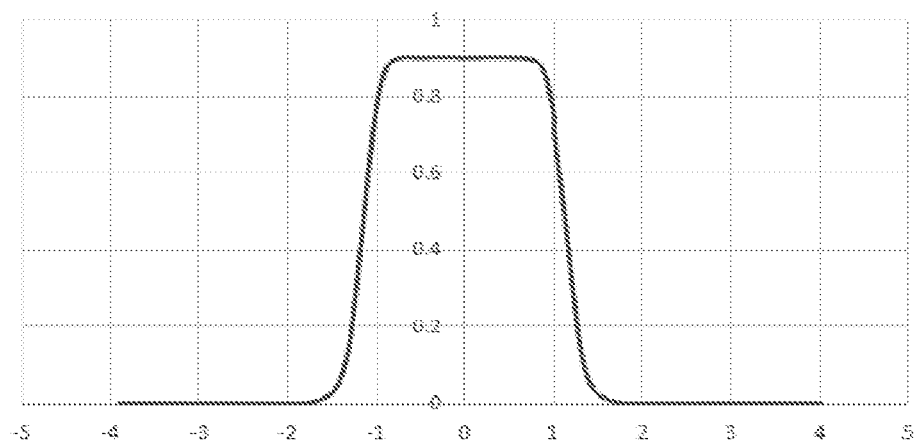
FIG. 4 shows a schematic view of the distribution of scattered light of a first light source passing through a diffusion sheet according to the first embodiment of the invention.

In the embodiment, the diffusion sheet 12 is arranged such that the laser beam emitted from the first light source 111 is effectively diffused within a certain angle. When the laser beam emitted from the first light source 111 reaches the dichroic mirror 13 through the diffusion sheet 12, it has a certain diffusion. Preferably, the FWHM (full width at half maximum) of the diffusion sheet 12 is 2-5°, most preferably 2-3°. The diffusion sheet can be a processed frosted glass sheet or a DOF (Diffractive optical element), such as a holographic grating, a phase grating, etc., such that the scattered light passing through the diffusion sheet 12 has a flat-top distribution (as shown in FIG. 4), rather than the form of a typical Lambertian reflector, so that the light intensity can be evenly distributed within a certain angle.

The dichroic mirror 13 is dichroic mirror allowing light of long wavelength passing through. By adjustment of reflectance, the dichroic mirror 13 enable a part of the laser beam to be reflected on the dichroic mirror 13, pass through the first collimating lens 141 and reach the fluorescent disc 15, and other part to pass through the dichroic mirror 13 and through the second collimating lens 142 to reach the reflective diffusion disc 16.

The laser beam reflected by the dichroic mirror 13 passes through the first collimating lens 141 and reach the fluorescent disc 15, and wavelength conversion occurs on the fluorescent disc 15, where the laser beam is converted into a light of longer wavelength. The converted light passes through the dichroic mirror 13 again after passing through the first collimating lens 141 to reach the other side of the dichroic mirror 13. Due to the arrangement of the diffusion sheet 12, the laser beam can be more uniformly irradiated onto the fluorescent disc 15, so that the fluorescent disc 15 can be excited by a higher-intensity light without quenching, producing a long-wavelength light of higher energy density, which in turn increases the luminance of white light illuminating device.

The laser beam passing through the dichroic mirror 13 passes through the second collimating lens 142 and reaches the reflective diffusion disc 16. The reflected light passes through the second collimating lens 142 again and reaches the dichroic mirror 13, where it can be reflected by the dichroic mirror 13 and combined with the long-wave light passing through the dichroic mirror 13 to form an acceptable visible light to enter the lens coupling unit 20.

In this embodiment, each of the first collimating lens 141 and the second collimating lens 142 can be a convex lens.

According to the embodiment, preferably, the dichroic mirror 13 provides a transmittance of 10%-40% for the light beam emitted from the first light source 111, which is preferably a 450 nm blue laser beam, so that the energy ratio between the long-wavelength light converted by the fluorescent disc 15 and the short-wavelength light reflected by the reflective diffusion disc 16 is within a suitable range.

Further, the reflective diffusion disc 16 has the same scattering performance as the fluorescent disc 15, and preferably, the reflective diffusion disc 16 and the fluorescent disc 15 are diffuse reflectors having a scattering angle of $\theta\frac{1}{2}=60°$.

Referring to FIG. 2, in the embodiment, the fluorescent disc 15 can be an annular disc having a plurality of light-emitting zones 151 arranged along the circumferential direction of the annular disc, and each of the light-emitting zones 151 can be coated with red, green, yellow or pure scattering mirror. When the fluorescent disc 15 is rotated, by time division multiplexing, the spectral component ratios can be adjusted to obtain white or even blue light presenting different color temperatures to expand the range of use.

It can be understood that the fluorescent disc 15 can also be immobilized. In this case, the fluorescent disc 15 can be coated with red and green phosphors.

In other embodiments, the fluorescent disc 15 is immobilized, and the fluorescent disc 15 can be coated with red-yellow phosphor. In this case, the yellow fluorescent material is mixed with the red fluorescent material or does not mix to form two layers. In a specific use, the mixed red-yellow fluorescent material can be mixed again with a transparent inorganic material (such as silicon oxide, titanium oxide, etc.) to form a uniform layer, and then calcined at a high temperature to form an inorganic fluorescent layer.

Further, a cooling baseplate 17 is further set on the fluorescent disc 15, and the fluorescent disc 15 is fixed on the cooling baseplate 17. Preferably, the cooling baseplate 17 is an aluminum cooler, a liquid cooler, a Peltier element or a heat pipe.

Referring to FIG. 3, according to the embodiment, the lens coupling assembly 20 comprises a first converging lens 211, a second converging lens 212, a light homogenizing rod 22, and a conductive optical fiber 23. The first converging lens 211, the second converging lens 212, the light homogenizing rod 22 and the conductive optical fiber 23 are arranged in sequence along the direction of light transmission, and the axes of the first converging lens 211, the second converging lens 212, the light homogenizing rod 22, and the conductive fiber 23 are on the same straight line.

The relatively scattering light emitted from the light source assembly 10, after having the light path changed by the first converging lens 211 and the second converging lens 212, can project light spot on the end face of the light homogenizing rod 22. The light homogenizing rod 22 can make the uneven light that may present at the converged light spot homogenized, such that the energy of the light collected by each of the optical fibers in the conductive optical fiber 23 is similar, improving the lateral uniformity of the outgoing beam.

As shown in FIG. 3, $\alpha$ is a divergence angle of an outgoing light beam from the light source assembly 10, and $\theta$ is a convergence half angle of the light beam after passing through the first converging lens 211 and the second converging lens 212. The Etendue of the light beam emitted from the light source assembly 10 is $\pi S(NA)^2$, where S is the effective irradiation area of the phosphor, $NA=\sin \alpha$; and the Etendue of the optical fiber is $\pi A(NA)^2$, where A is the cross-sectional area of the fiber, $NA=\sin \theta$. Preferably, the Etendue of the light beam emitted from the light source assembly 10 is less than or equal to the Etendue of the conductive optical fiber 23 to reduce the loss of light.

Further, the light beam emitted from the light source assembly 10 passes through the first converging lens 211 and the second converging lens 212, and reach the end of the light homogenizing rod 22 away from the conductive optical fiber 23. The converged light spot of the reached light beam is less than or equal to the end surface area of the conductive optical fiber 23, and/or the convergence half angle of the reached light beam is less than or equal to the collection angle of the conductive optical fiber 23, to improve the lateral energy distribution of the light beam that converges on the end face of the fiber.

According to the embodiment, the cross section of the light homogenizing rod 22 is a circle matching the cross-section of the conductive optical fiber 23. That is, the cross section of the light homogenizing rod 22 and the conductive optical fiber 23 are both cross-sectional circular and of the same radius. The light homogenizing rod 22 can be a solid cylindrical glass rod, preferably a quartz rod or a material with same or similar index of refraction with the conductive optical fiber 23. Further, when the light homogenizing rod 22 is a quartz rod, a high-reflection film is coated on the outside of the light homogenizing rod 22, and in practical use, the light homogenizing rod 22 can be arranged in a hollow tube, and the high-reflection film is attached to the inner wall of the hollow tube.

Further, according to the embodiment, a protective glass window 24 is further arranged at an end of the light homogenizing rod 22 near one end of the second converging lens 212. Since only cold light source is used in the light source assembly 10, with no infrared component, the protective glass window 24 can be a common optical glass window such as K9 or quartz, which can improve the light transmittance as compared with the conventional heat insulating sheet which works by reducing the infrared transmittance.

According to the embodiment, by the arrangement of the diffusion sheet 12, the light beam emitted from the first light source 111 can be uniformly scattered, so that the fluorescent disc 15 can be excited by the light source of higher luminance without quenching, which can product long-wavelength light of higher energy density, and in turn increase the luminance of the white light illuminating device. Further, by limiting the transmittance of the dichroic mirror 13, the energy ratio between transmitted beam and reflected beam of the outgoing beam from the first light source 111 can be controlled on the dichroic mirror 13, which can improve the quality of the light. Further, by the arrangement of the first converging lens 211, the second converging lens 212 and the light homogenizing rod 22, the light guiding efficiency can be improved, and the loss of light energy can be reduced.

Figure 5:
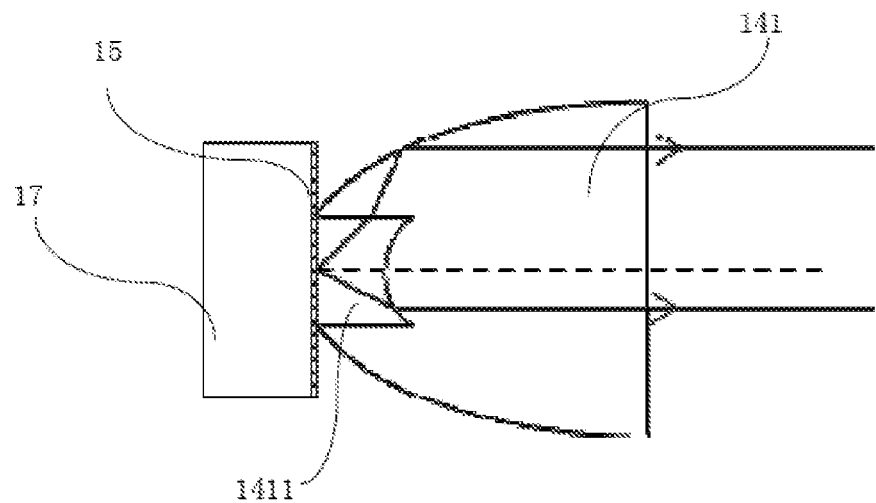
FIG. 5 shows a structural view of a fluorescent disc and a first converging lens according to the second embodiment of the invention.

FIG. 5 shows a structural view of the fluorescent disc and the first converging lens according to a second embodiment of the invention. As shown in FIG. 5, the illuminating device provided by the invention in the second embodiment is substantially the same as the illuminating device provided in the first embodiment. The difference is that, in the second embodiment, the first collimating lens 141 is a cup-shaped lens in cross section, comprises an inner cylindrical recess 1411 at a side of the first collimating lens 141, said side facing the fluorescent disc 15, a bottom of the inner cylindrical recess 1411 protruding toward the fluorescent disc 15 to form an arc surface. The axis of the first collimating lens 141 and the axis of the inner cylindrical recess 1411 are both located on the optical axis of the dichroic mirror 13 after reflection. Referring to the optical path shown in FIG. 5, the light beam reflected by the dichroic mirror 13, after wavelength conversion by the fluorescent disc 15 and light path change by the first collimating lens 141, can pass through the first collimating lens 141 in a state of parallel light. The first collimating lens 141 can be an optical plastic such as PMMA (polymethyl methacrylate).

It can be understood that the form of the above converging lens can also be applied to the second collimating lens 142.

Figure 6:
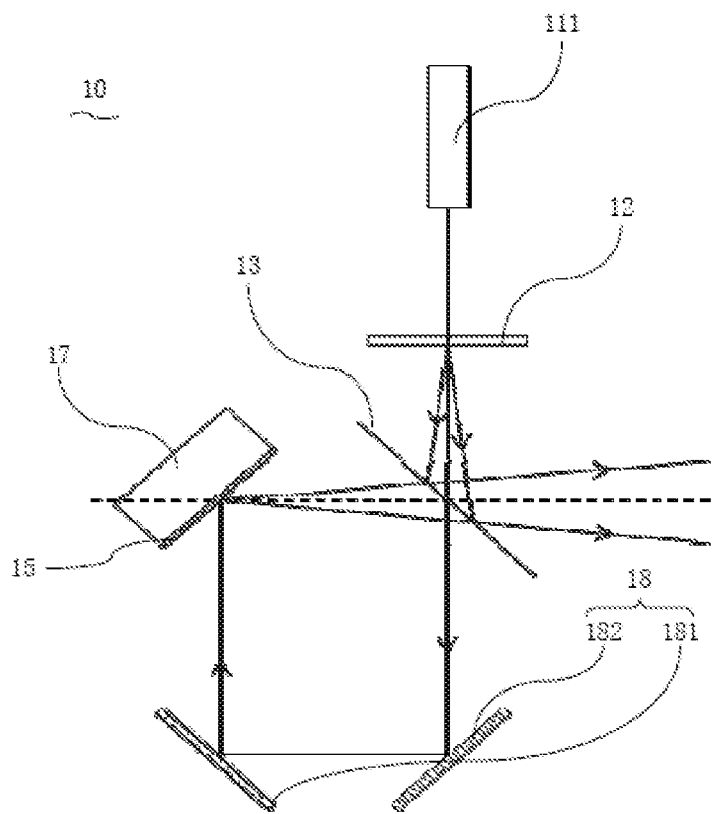
FIG. 6 shows a structural view of a light source assembly of the illuminating device according to the third embodiment of the invention.
Figure 7:
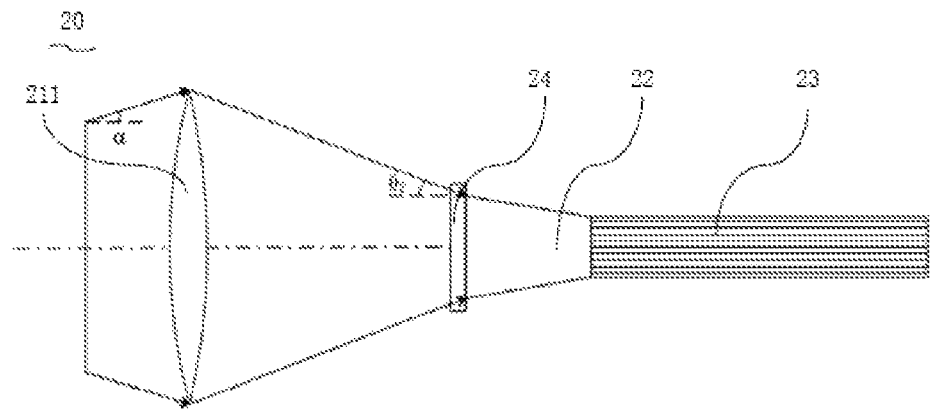
FIG. 7 shows a structural view of a lens coupling assembly of the illuminating device according to the third embodiment of the invention.

FIG. 6 shows a structural view of the light source assembly of the illuminating device according to the third embodiment of the invention, and FIG. 7 shows a structural view of the lens coupling assembly of the illuminating device according to the third embodiment of the invention. Referring to FIG. 6 and FIG. 7, the light source assembly 10 according to the third embodiment of the present invention comprises a first light source 111, a diffusion sheet 12, a dichroic mirror 13, a reflecting mirror 18, and a fluorescent disc 15. The diffusion sheet 12 is arranged between the optical paths of the first light source 111 and the dichroic mirror 13. The dichroic mirror 13 is arranged obliquely relative to the optical axis of the first light source 111, preferably at an angle of 45°. The fluorescent disc 15 and the reflecting mirror 18 are arranged on the other side of the dichroic mirror 13 relative to the first light source 111.

A small hole (not shown in FIG. 6) is cut in the dichroic mirror 13, and preferably, the small hole has a diameter of 1-5 mm. The small hole is located on the optical axis of the first light source 111, and part of the light from the first light source 111 is incident on the other side of the dichroic mirror 13 through the small hole, and other portions of the light are reflected by the dichroic mirror 13. The reflecting mirror 18 works with the fluorescent disc 15, to make the light passing through the small hole reach the fluorescent disc 15 by the reflection of the reflecting mirror 18, and is again incident on the dichroic mirror 13 after conversion of wavelength on the fluorescent disc 15.

According to the embodiment, due to the arrangement of the diffusion sheet 12, when the light from the first light source 111 is incident on the dichroic mirror 13, a light spot is generated on the dichroic mirror 13 due to scattering. The light from the first light source 111 is reflected by the dichroic mirror 13, and part of the light passing through the small hole will pass through the dichroic mirror 13, and the light passing through the dichroic mirror 13 can be incident on the fluorescent disc 15 under the action of the reflecting mirror 18. The light re-emitted from the fluorescent disc 15 with wavelength converted can pass through the dichroic mirror 13, and then combine with the light initially reflected by the dichroic mirror 13 into the desired visible light which enters the lens coupling assembly 20 for light coupling.

Further, in order to enable better light combination, according to the embodiment, the fluorescent disc 15 has a certain scattering property, and preferably, the fluorescent disc 15 enables the wavelength-converted light to have a scattering angle of ±20°.

In this embodiment, the first light source 111 can be a blue laser light source, and the fluorescent disc 15 is coated with a red-green phosphor or a red-yellow phosphor. A cooling baseplate 17 is also provided on the fluorescent disc 15.

According to this embodiment, the reflecting mirror 18 comprises a first plane mirror 181 and a second plane mirror 182. The dichroic mirror 13, the first plane mirror 181, the second plane mirror 182, and the fluorescent disc 15 are arranged sequentially along the optical path, and the first plane mirror 181 is arranged below the dichroic mirror 13 and at an angle of −45° with the optical axis of the first light source 111 (take the counterclockwise direction as positive). The second plane mirror 182 is arranged on the optical path of the first plane mirror 181 after reflection and is at an angle of 45° with the optical axis of the first light source 111. That is, the angle between the first plane mirror 181 and the second plane mirror 182 is a right angle. The extending direction of the second plane mirror 182 is parallel to the dichroic mirror 13. The fluorescent disc 15 is arranged on the optical path of the second plane mirror 182 after reflection, and is at an angle of −45° with the optical axis of the first light source 111. That is, the fluorescent disc 15 is parallel to the first plane mirror 181. The optical axis of the light emitted from the fluorescent disc 15 with wavelength converted passes through the small hole of the dichroic mirror 13 and is perpendicular to the optical axis of the first light source 111.

In order to enable the light rays on both sides of the dichroic mirror 13 to be better combined, the diffusion sheet 12, the dichroic mirror 13, the fluorescent disc 15 and the reflecting mirror 18 cooperate to make the light spot from the fluorescent disc 15 on the dichroic mirror 13 fit in size with the light spot from first light source 111 on the dichroic mirror 13.

It can be understood that in this embodiment, the first plane mirror 181 and the second plane mirror 182 can be replaced by right angle prisms to increase the integration performance of the entire device.

Compared with the first embodiment, in this embodiment, by the arrangement of the diffusion sheet 12 and the small hole on the dichroic mirror 13, the light emitted from the first light source 111 can be partially reflected by the dichroic mirror 13 and the other can pass through the dichroic mirror 13 to reach the fluorescent disc 15, which in turn facilitates the combination of light, simplifies the structure of the light source assembly 10, and also makes the optical path simpler and reduces the loss of light energy. In the other aspect, the structure described above can control the divergence angle α of the light emitted from the light source assembly 10 by controlling the scattering angle of the diffusion sheet 12 and the fluorescent disc 15, so as to facilitate the subsequent layout of the lens coupling assembly 20.

Referring TO FIG. 7, according to this embodiment, the lens coupling assembly 20 comprises a first converging lens 211, a light homogenizing rod 22, and a conductive optical fiber 23, and the first converging lens 211, the light homogenizing rod 22, and the conductive optical fiber 23 are arranged in order along the direction of light transmission. The light converged by the first converging lens 211 enters the light homogenizing rod 22.

Compared with the first embodiment where the first converging lens 211 and the second converging lens 212 are arranged, in the second embodiment, only the first converging lens 211 is used to obtain a larger converging spot and a smaller convergence half angle $\theta_2$, which can maintain a good lateral illumination distribution and reduce the cost of the entire device.

In order to accommodate a solution having only one converging lens, in the second embodiment, the light homogenizing rod 22 is tapered, has a reducing diameter from the end far from the conductive optical fiber 23 to the end close to the conductive optical fiber 23. The diameter of one end of the light homogenizing rod 22 close to the conductive optical fiber 23 is the same as the diameter of the end surface of the conductive optical fiber 23. The material of the light homogenizing rod 22 is the same as that in the first embodiment, and the details are not described herein.

A protective glass window 24 is also provided at the end of the light homogenizing rod 22 near the end of the first converging lens 211. The material of the protective glass window 24 is the same as that in the first embodiment, and details are not described herein.

It should be noted that the light source assembly 10 in the second embodiment can be combined with the lens coupling assembly 20 in the first embodiment, and the lens coupling assembly 20 in the second embodiment can also be combined with the light source assembly 10 in the first embodiment. The combination of the two assemblies in the two embodiments is not limited by others.

Figure 8:
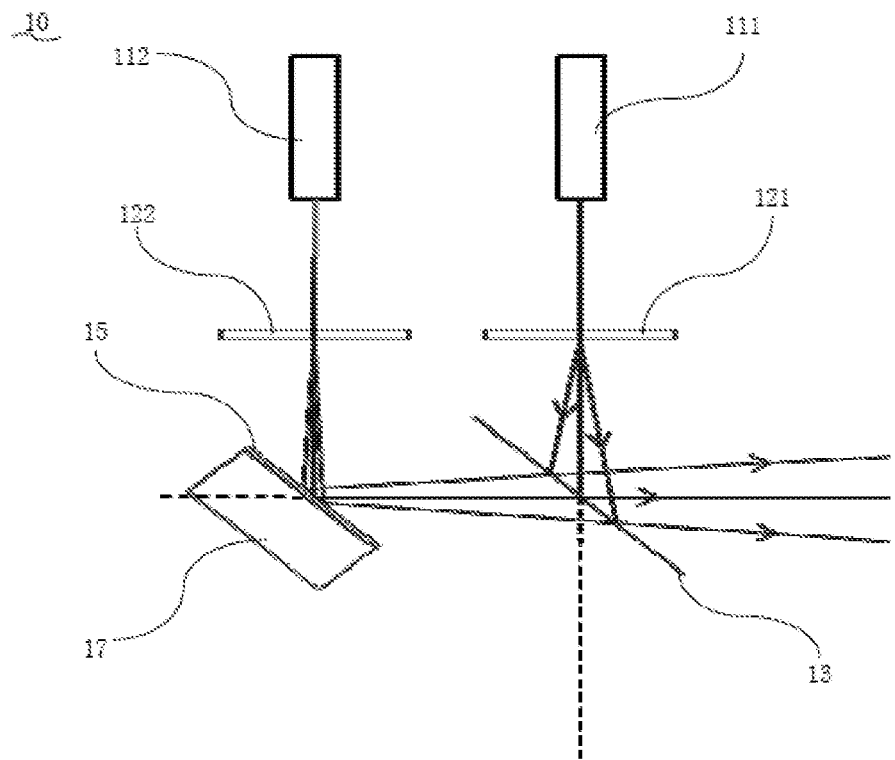
FIG. 8 shows a structural view of a light source assembly of the illuminating device according to the fourth embodiment of the invention.

FIG. 8 shows a structural view of a light source assembly according to a fourth embodiment of the invention. As shown in FIG. 8, the light source assembly 10 of the embodiment comprises a first light source 111, a first diffusion sheet 121, a second light source 112, a second diffusion sheet 122, a fluorescent disc 15, and the dichroic mirror 13. The first diffusion sheet 121 is arranged between the first light source 111 and the dichroic mirror 13. The light emitted from the first light source 111 passes through the diffusion sheet 121 and reaches the dichroic mirror 13 where the light can be reflected. The dichroic mirror 13 is arranged obliquely relative to the optical axis of the first light source 111, preferably at 45°.

The second light source 112, the second diffusion sheet 122, and the fluorescent disc 15 are sequentially arranged along the optical path of the second light source 112. The second diffusion sheet 122 is arranged between the second light source 112 and the fluorescent disc 15, and the light emitted from the second light source 112 reaches the fluorescent disc 15 after passing through the second diffusion sheet 122. The light emitted from the fluorescent disc 15 passes through the dichroic mirror 13 from the side opposite to the first light source 111, and combines with light from the first light source 111 into the desired visible light. The second light source 112, the fluorescent disc 15 and the dichroic mirror 13 cooperate to make the optical axis of the light emitted by the fluorescent disc 15 is perpendicular to the optical axis of the first light source 111.

According to this embodiment, the first light source 111 may be a blue laser light source or an LED light source, and the second light source 112 may be a laser light source such as blue light, violet light or ultraviolet light.

According to this embodiment, in order to better combine the light, preferably, the first diffusion sheet 121, the second diffusion sheet 122, and the fluorescent disc 15 cooperate in scattering property and position to make the light spot from the second light source 112 on the dichroic mirror 13 fit in size with the light spot from the first light source 111 on the dichroic mirror 13. That is, the scattering angle of the first diffusion sheet 121 is larger than the scattering angle of the second diffusion sheet 122. On the basis of this, the larger the scattering angle of the second diffusion sheet 122, the smaller the scattering angle of the fluorescent disc 15, and the smaller the scattering angle of the second diffusion sheet 122, the larger the scattering angle of the fluorescent disc 15.

According to the solution provided by the embodiment, the brightness of the light emitted by the light source unit 10 can be easily improved by the arrangement of the two light sources and the two diffusion sheets 12, and the light color can be easily adjusted to meet various needs.

In summary, the present invention can uniformly disperse the light beam emitted from the first light source 111 by the arrangement of the diffusion sheet 12, so that the fluorescent disc 15 can be excited by the higher luminance light source without quenching, and can generate a long-wavelength light of higher energy density, in turn, increases the luminance of the white light illuminating device. Further, by the arrangement of the first converging lens 211 and the homogenizing rod 22, it is possible to have a high light guiding efficiency and reduce the loss of optical energy.

The present invention also provides an endoscope comprising the illuminating device provided by the present invention. For other technical features of the endoscope, please refer to the prior art, and details are not described herein. In this embodiment, the endoscope further comprises a CMOS (Complementary Metal-Oxide-Semiconductor) sensor, and the illuminating device that uses laser to excite the phosphor to obtain a high-luminance light source can compensate for the defect of poor imaging quality of the CMOS sensor under low illumination, and effectively reduce the noise of the CMOS sensor under the support of high-luminance light source to realize the application of the CMOS sensor in the endoscope.

It will be appreciated by those skilled in the art that the above discussion is for demonstration purpose; and the examples discussed above are some of many possible examples. Other variations are also applicable.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain method procedures may have been delineated as separate procedures; however, these separately delineated procedures should not be construed as necessarily order dependent in their performance. That is, some procedures may be able to be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments, however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. As used in this disclosure, the term "preferably" is non-exclusive and means "preferably, but not limited to." Terms in the claims should be given their broadest interpretation consistent with the general inventive concept as set forth in this description. For example, the terms "coupled" and "connect" (and derivations thereof) are used to connote both direct and indirect connections/couplings. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended". Claims are not intended to be interpreted under 112 sixth paragraph unless the phrase "means for" and an associated function appear in a claim and the claim fails to recite sufficient structure to perform such function.

What is claimed is:

1. An illuminating device, comprising:
   a light source assembly, the light source assembly comprising a first light source, a diffusion sheet and a dichroic mirror;
   wherein the diffusion sheet is disposed between the first light source and the dichroic mirror, and the diffusion sheet is used to diffuse light of the first light source;
   wherein the light source assembly further comprises a first collimating lens, a second collimating lens, a fluorescent disc, and a reflective diffusion disc;
   wherein
   the dichroic mirror is disposed obliquely relative to the optical axis of the first light source;
   the fluorescent disc and the first light source are disposed at the same side of the dichroic mirror;
   the first collimating lens is disposed between the light paths of the fluorescent disc and the dichroic mirror;
   the reflective diffusion disc and the first light source are respectively located at opposite sides of the dichroic mirror; and the second collimating lens is arranged between the light paths of the dichroic mirror and the reflective diffusion disc;

wherein the first collimating lens and/or the second collimating lens is a cup-shaped lens in cross section, comprising an inner cylindrical recess at a side of the first or second collimating lens, said side facing the fluorescent disc or the reflective diffusion disc, a bottom of the inner cylindrical recess protruding toward the fluorescent disc or the reflective diffusion disc to form an arc surface.

2. The illuminating device of claim 1, wherein the FWHM of scattering angle of the diffusion sheet is 2-5°, and the scattering of light from the first light source passing through the diffusion sheet has a flat top distribution.

3. The illuminating device of claim 1, wherein
the dichroic mirror is at an angle of −45° to the optical axis of the first source;
the optical axis of the first collimating lens is perpendicular to the optical axis of the first light source; and
the optical axis of the second collimating lens is on the same straight line as the optical axis of the first light source.

4. The illuminating device of claim 1, wherein the first collimating lens and/or the second collimating lens is a convex lens.

5. The illuminating device of claim 1, wherein
the arrangement of the dichroic mirror makes a part the light beam from the first light source reflected by the dichroic mirror and other part from the first light source passing through the dichroic mirror;
the light beams reflected by the dichroic mirror is directed to the fluorescent disc through the first collimating lens; and
the light beam beams passing through the dichroic mirror is directed to the reflective diffusion disc through the second collimating lens.

6. The illuminating device of claim 5, wherein the dichroic mirror has a transmittance of 10%-40% for the light beams from the first light source.

7. The illuminating device of claim 1, wherein the first light source is a blue laser light source.

8. The illuminating device of claim 2, wherein the fluorescent disc is an annular disc comprising a plurality of light-emitting zones arranged along the circumference of the annular disc, the lighting-emitting zones being coated with red, green and/or yellow fluorescent powder.

9. The illuminating device of claim 8, wherein the fluorescent disc is coated with red and green fluorescent powder or red and yellow fluorescent powder.

10. The illuminating device of claim 8, wherein the fluorescent disc is further provided with a cooling baseplate.

11. The illuminating device of claim 1 is part of an endoscope.

12. The endoscope of claim 11, wherein the endoscope further comprises a CMOS sensor.

* * * * *